United States Patent [19]

Jordan

[11] 4,255,453

[45] Mar. 10, 1981

[54] PRODUCTION OF ISOCYANIC ACID AND ISOCYANATES

[76] Inventor: Robert K. Jordan, Carlton House, Ste. 1431, 550 Grant St., Pittsburgh, Pa. 15219

[21] Appl. No.: 825,096

[22] Filed: Aug. 16, 1977

[51] Int. Cl.³ ..................... C01C 3/14; C07C 118/00
[52] U.S. Cl. ................................ 423/365; 204/158 R; 260/429 R; 260/438.1; 260/439 R; 260/453 P; 260/453 PC; 544/193; 544/221; 562/433; 562/555; 562/609
[58] Field of Search ..................... 260/453 PC, 453 P; 423/365

[56] References Cited

U.S. PATENT DOCUMENTS

| | | | |
|---|---|---|---|
| 3,314,754 | 4/1967 | Godfrey | 423/365 X |
| 3,734,941 | 5/1973 | Sydor | 260/453 P |
| 3,919,279 | 11/1975 | Rosenthal et al. | 260/453 P |
| 4,133,868 | 1/1979 | Jordan | 260/453 P X |

*Primary Examiner*—Dolph H. Torrence

[57] ABSTRACT

A process for the production of isocyanates by the addition of carbon monoxide to a metal or aryl carbamate.

6 Claims, No Drawings

PRODUCTION OF ISOCYANIC ACID AND ISOCYANATES

This invention relates to a process for combining carbon monoxide to metal salt of carbamic and N-mono organic carbamic acids to produce isocyanates, homopolymers and adducts.

Isocyanates and isocyanic acid are intermediates used mostly in plastics. Toluene diisocyanate isomers are mixed with polyols, of OH numbers 25–70, in the presence of water, a blowing agent and a catalyst to produce flexible polyurethane foams. Polymethylenepolyphenyleneisocyanates and polyols of OH numbers 200–1000 are similarly compounded, but without water, to produce rigid polyurethane foams. Hexamethylenediisocyanate is catalytically reacted with linear diols to produce polyurethane elastomers for outerwear. Methyl isocyanate is added to alpha-naphthol to produce the ester which is a well known pesticide. Cyanurate metal salts, by the base polymerization of isocyanic acid, are chlorinated to produce germicides. Isocyanated are produced by the phosgenation of the corresponding amines, a hazardous process consuming expensive chlorine and making relatively useless by-product hydrogen chloride in an energy intensive process.

Therefore, it is an object of my invention to provide a new and improved process for the production of isocyanates.

My invention is a process for the production of isocyanates and homopolymers and adducts thereof with components from carbon monoxide adducts, comprising combining a metal N-mono organic carbamate and carbon monoxide.

I have discovered that metal carbamates containing an allophanate hydrogen atom are converted to isocyanates evidentally by the mechanism,

$RNHCO_2M \rightleftharpoons RNCO + HOM$ and
$HOM + CO \rightarrow HCO_2M$ in which some degree of dissociation results in a transient formation of the hydroxide which then adds to carbon monoxide, normally producing the metal formate. Of course it could well be that the carbon monoxide adds to the N—H bond followed by rearrangement. Since all metals appear to have stable formates, however the mechanism, the result is the production of the isocyanate from metal carbamates. Salts of metals which, as such or whose compounds tend to catalyze carbon monoxide additions, combine especially easily. These include the transition and noble metal salts such as palladium, cobalt, iron, iridium, etc., although economics and commercial considerations dictate the alkali and alkaline earth metal salts including sodium, calcium, potassium and magnesium as most desirable.

All metal salts of the carbamic acids tested worked in the process including alkali, alkaline earth, transition and noble metal salts. And some have in themselves catalytic and cocatalytic effects on the process, in fact the effectiveness of the catalysts depends on the salt. The metal salts tried included sodium, potassium, magnesium, copper, iron, aluminum, titanium and palladium; probably all work.

The process can be conducted in the absence of a solvent or liquid media, but proceeds smoothly in any inert nonaqueous media and even such media that have a tendency to slightly react. Thus hydrocarbons, for example benzene, ethers such as ethyl ether and tetrahydrofuran, polyethers like 18-crown-6 and alkoxy or acyl terminated polyethylene oxides, esters like methyl benzoate, amides including dimethyl acetamide, halogenated hydrocarbons including chlorinated benzene and tetrachloroethylene, ketones and many others.

The temperature of the process may range greatly since the metal carbamates are fairly stable and is mainly dependent on the catalyst system employed and the residence time. Ideally the process is conducted at from about 50° C. to 250° C., although as noted with shorter residence times the temperature may range upwards of 350° C. until under the conditions of the process undesirable decomposition levels are suffered. The pressure may range from about atmospheric pressure to 1000 atmospheres, but ideally up to about 100 atmospheres. Since carbon monoxide is a gas the proportions of reactants are meaningless. However the carbon monoxide may range in concentration from 1 to 100 percent, diluted by a number of diluents which do not interfere or only slightly interfere with the process. Again this in part depends on the catalyst employed, but normally includes nitrogen, carbon dioxide and even hydrogen. Thus carbon monoxide in the form of blast furnace top gas, oxygen-blown blast furnace top gas, basic oxygen furnace gas, reformed natural gas and gas from the partial oxygen or air combustion of coke and coals and shales may be used.

The catalysts include metal carboxylates of transition and noble metals, metal carbonyls, hydrocarbyl metal carbonyls and metal carbonyls and their substituted analogs such as trifluorophosphine and cyano complexes, and the simple compounds of these metals including the halides. Some of the more ideal catalysts include palladium and its compounds including acetate, chlorides and complexes; selenium and its compounds including the oxide, oxychloride and disulfide; and with these basic promoters are optionally used because in turns out that in addition to tertiary amines such as pyridine, they can include the carbamate salts themselves of basic acetates, etc. Metal halides and other halide compounds such as fluoroborates, fluorphosphates and like compounds are not only promoters but often catalysts themselves. Some metals or compounds thereof useful as catalysts and, cocatalysts include for examples iridium, rhodium carbonyls, tellurium sulfide, lead chloride mercury acetate, arylmolybdenumtricarbonyl, cobalt carbonyl, copper I and II acetates and chlorides, barium carboxylates, ferromanganese, complex tin carbonyls, ferric chloride and antimony hexafluoride compounds. Clearly there is a tremendous range of catalysts useful in the process and a myriad of cocatalysts that may be used to promote the process in addition to the cations of the carbonyls acids, which as already noted are often selected on the basis of their catalytic ability as obviously the various cations in the aforementioned catalysts may easily be the cations of the carbamic acid salts. Generally the catalysts known in the catalytic addition of carbon monoxide to alcohols, olefins, amines, etc have a catalytic effect on the instant process.

Radiation, especially gamma, beta and ultraviolet light can cattalyze or promote the process and this might be expected since for example, gamma irradiation from $Co^{60}$ catalyzes the addition of carbon monoxide to ammonia to form formamide, it is even better as a "cocatalyst" to alkali metal alkoxides and is also by itself a very excellent catalyst for the production of copolymers of high molecular weight. Using untraviolet light sensitizers should be employed. A number of metal alkoxides and bases act to catalyze the process, but also under certain conditions cause polymerization of one kind or another of the isocyanates themselves for example potassium alkoxides and tetraalkyl guanidines. Crown ethers are promoters.

Metal carbamates may be made by a number of methods. One by my recently issued patent, U.S. Pat. No. 4,034,037 of July 5, 1977 that is entitled "Carboxylation Metallation Process", in which a primary amine and a metal salt is carbonated in an appropriate solvent. For example methyl amine and sodium chloride in liquid ammonia is treated with carbon dioxide to precipitate sodium N-methyl carbamate. The classical way for their preparation entails treatment of the amine with metallic sodium or potassium followed by carbonation of the N-alkali metal intermediate and an example it is the use of aniline to make the corresponding sodium carbanilate. Another interesting method is especially applicable to the products of Netherlands application Ser. No. 75 02,156 of May 30, 1975 to Atlantic Richfield Company which produced for example methyl N-phenyl carbamate from nitrobenzene, methanol and carbon monoxide using a selenium compound, e.g., $SeO_2$. By treating the ester with sodium hydroxide or other metal hydroxide, in a solvent, for example methanol, the metal salt of N-phenyl carbamate is obtained. For producing the metal salts of metals which do not have sufficiently strong hydroxide or none at all the metal salt of a weaker acid than carbamic acid, or of an acid which is especially volatile may be employed. Thus by this or the technology of my copending application practically every metal salt can be obtained.

Commercially the important isocyanates are those of the metal salts of N-substituted methyl carbamic, hexamethylenedicarbamic, mixed isomers of toluenedicarbamic, methylene bis(4-carbanilic) and polymethylenepolyphenylenecarbamic acids. But the process is not limited to those since the alkyl, alkylene, aryl and arylene compounds may contain inert or relatively inert substituents such as halo, nitrile, alkoxy, acyl and other radicals. Examples include metal salts of N-xylylidenedicarbamic and N-4-fluorophenylcarbamic acids. The metal salts of methylene bis(dicarbamic acid) is of interest because of the ease of their production. While it is believed that every metal salt may be produced those of greatest immediate import are the alkali, alkaline earth, transition and noble metal salts, ideally the alkali metal salts.

Ideally the process is conducted continuously. One especially favorable arrangement utilizes a vertical tubular reactor where the carbon monoxide is fed at the bottom through a countercurrent liquid flow in which the metal carbamate is dissolved in a solvent which also premits the use of a column packing to increase contact. For volatile cyanic acid, HNCO, even under considerable pressure, it may be taken off the top of the column. Likewise with methyl or ethyl isocyanates, both of which boil at about 60° C. But most of commercial isocyanates have relatively high boiling points and as a result it is best to continuously take off solution or slurry from the bottom and take off the isocyanate in a separate chamber or column, still continuously, at atmospheric or reduced pressure down to a minute fraction of an atmosphere. If then the metal carboxylate formed is not soluble in the media it can be filtered off before or after the isocyanate is removed. If it is soluble, the media selected would presumably be of such volatility as not to interfere with the distillation of the isocyanate.

As the metal carbonyl often have considerable volatility its gaseous mixture with relatively pure carbon monoxide may be used as a fluidizing media for the solid metal carbamates, or the metal carbamates may be dropped through the gas. The isocyanates being distilled simultaneously or afterwards, and the solid metal carboxylate collected at the bottom. However conducted if the isocyanate is a polymeric isocyanate incapable of distillation, it should be separable from the metal carboxylate ideally by filtration or by centrifuging. But of course as the metal carboxylate is almost universally metal formates. Yet acylfluorides may be added to produce other metal salts, as noted earlier herein. Isocyanates being stable to many such acids, if desired the whole of the reaction product may be treated with other non-interefering acids to corresponding metal salts and the isocyanate, especially if separation is facilitated.

The metal formates can be important economically to the process as also it is well known that anhydrous sodium formate is commercially fused at about 400° C. under a short residence time to produce sodium oxalate with the evolution of hydrogen. But other metal formates are important for other reasons, for example copper and nickel formates thermally decompose to the metal powders at less than 400° C. The calcium and other salts thermally decompose at about the same temperature to provide formaldehyde, and, such a process for relatively high yields may be developed. Iron and cobalt and other metal powders can be made by the thermal decomposition of the metal formates in an atmosphere containing hydrogen. As noted, some of the transition metal carbamate salts have a catalytic effect on the process and to an extent this can govern the selection of the metal salt used.

Lynn and Singleton have shown that formate esters decompose under catalytic conditions to produce carbon monoxide and methanol in U.S. Pat. No. 3,716,619. Likewise it is known that metal carbonyls themselves decompose to produce carbon monoxide. Clearly then, such adducts of carbon monoxide as decompose under the conditions of the process such as methyl formate, dimethyl formamide, etc to produce carbon monoxide and a compound containing a labile hydrogen atom produce adducts of the isocyanates, for examples the corresponding methyl ester of the carbamic acid, or the corresponding urea, etc.

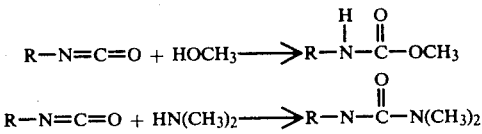

In both instances of the examples, the decomposition of the methyl formate to methanol and dimethyl formamide to dimethyl amine as coproducts to carbon monoxide can be catalyzed by the same or different catalysts.

Other adducts of carbon monoxide which decompose to carbon monoxide and compounds that aid, or which do not significantly interfere to the extent of forming isocyanate adducts include acyl fluorides, metal carbonyls, dialkyl oxalates, carbonyl sulfide, etc.

Finally it was earlier noted that especially under certain basic catalysts that the isocyanates tended to polymerize and it is well known that without stabilizers even under neutral conditions they polymerize. No doubt many of the catalysts useful in the process will tend to polymerize the isocyanates in different ways. The nature of the polymers formed is best explained using isocyanic acid as the example. It is especially economically made by the instant process since it is well know that many metal salts of carbamic acid can be made by dissolving a metal salt in liquid ammonia and then simply bubble in carbon dioxide to precipitate the metal salt of carbamic acid, $H_2NCO_2M$. By this and other techniques the metal salts include those of mono-, bi-, tri- and tetravalent metals just as the same metal salts of mono-organic substituted carbamic acids are made and used. Then in the process isocyanic acid is the initial product which may be said to have two structures, via the tautomeric system;

H—O—C≡N  O=C=N—H whatever, it is unstable above 0° C. so in practice once formed its vapors would ideally be rapidly cooled to below 0° C. But it tends to polymerize even under neutral or somewhat acidic conditions and especially under basic conditions, the latter "aldol" to cyanuric acid structure which again is a tautomeric system. The other structure is that of cyamelide from "aldehyde" polymerization. The polymerization under basic conditions is especially rapid and potassium cations especially are catalytic. The conventional isocyanates such as aliphatic and aromatic isocyanates polymerize in several ways too, and in fact the isocyanurates are produced using especially basic catalysts and are characterized by exceptional thermal stability. Depending on the catalyst systems utilized, various polymers are produced and there is much literature on the nature of isocyanate polymerization under the influence of various catalysts.

According to the mechanism proposed it would be reasonable that carbamic acid esters that tend to dissociate, for example aromatic esters of N-methyl carbamic, toluene dicarbamic, xylylidenedicarbamic, methylene bis(4-phenylcarbamic), polymethylenepolyphenylenecarbamic and hexamethylenedicarbamic acids should likewise undergo formylation to produce the corresponding aryl formate and yield the isocyanate. And it turns out that such are easily carbonylated to formate esters, i.e., phenyl and naphthyl formate, and the corresponding isocyanates, for example the alpha-naphthyl ester of N-methyl carbamic acid yields methyl isocyanate, ideally at the temperature near where the aryl carbamate tends to dissociate to methyl isocyanate and alpha-naphthol. The same well known catalysts as employed for the process of combining a metal carbamate and carbon monoxide, preferably at 100° C. to 350° C. and one to 100 atmospheres.

According to the provision of the patent statutes, I have explained the principle of my invention and have illustrated and described what I now consider to represent its best embodiment. However, I desire to have it understood that within the scope of the appended claims, the invention may be practiced otherwise.

I claim:

1. A process for the production of isocyanates and homopolymers thereof comprising combining a metal N-mono organic substituted carbamate and carbon monoxide.

2. The process of claim 1 using a catalyst.

3. A process for the production of isocyanaic acid and homopolymers thereof comprising combining a metal salt of carbamic acid and carbon monoxide.

4. The process of claim 3 using a catalyst.

5. A process for the production of isocyanates and homopolymers thereof comprising combining an ester of carbamic or an N-mono organic substituted carbamic acid and carbon monoxide.

6. The process of claim 5 using a catalyst.

* * * * *